United States Patent [19]
Tanaka et al.

[11] Patent Number: 6,078,123
[45] Date of Patent: Jun. 20, 2000

[54] STRUCTURE AND METHOD FOR MOUNTING A SAW DEVICE

[75] Inventors: Kei Tanaka; Eiichi Fukiharu; Yasunori Tanaka; Michinobu Tanioka; Kenichi Otake; Takuo Funaya, all of Tokyo, Japan

[73] Assignee: NEC Corporation, Tokyo, Japan

[21] Appl. No.: 09/129,539

[22] Filed: Aug. 5, 1998

[30] Foreign Application Priority Data

Aug. 8, 1997 [JP] Japan ...................................... 9-214332

[51] Int. Cl.[7] .................................................. H01L 41/08
[52] U.S. Cl. ...................... 310/313 R; 310/344; 310/342
[58] Field of Search ................................ 310/313 R, 344, 310/348

[56] References Cited

U.S. PATENT DOCUMENTS

| 4,047,129 | 9/1977 | Ishiyama | 333/193 |
|---|---|---|---|
| 4,734,608 | 3/1988 | Takoshima | 310/313 R |
| 5,623,236 | 4/1997 | Yoshinaga et al. | 333/187 |
| 5,920,142 | 7/1999 | Onishi et al. | 310/313 R |

FOREIGN PATENT DOCUMENTS

| 0 805 552 A2 | 11/1997 | European Pat. Off. |
| 60-53058 | 3/1985 | Japan |
| 3272212 | 12/1991 | Japan |
| 4150405 | 5/1992 | Japan |
| 4369915 | 12/1992 | Japan |
| 10-163799 | 6/1998 | Japan |

*Primary Examiner*—Nestor Ramirez
*Assistant Examiner*—Peter Medley
*Attorney, Agent, or Firm*—Sughrue, Mion, Zinn, Macpeak & Seas, PLLC

[57] ABSTRACT

A structure for mounting a SAW (Surface Acoustic Wave) device includes photosensitive resin filling a gap between the SAW device and a mounting substrate in the peripheral portion of the SAW device. The entire structure is substantially as small in size as the SAW device and light weight. The photosensitive resin is formed in a region including pads for connection in order to absorb thermal stresses and extraneous forces apt to act on the pads. Second resin may surround the photosensitive resin or may be provided in a laminate structure together with the photosensitive resin so as to enhance a sealing ability. A method of mounting a SAW device is also disclosed.

12 Claims, 6 Drawing Sheets

STRUCTURE AND METHOD FOR MOUNTING A SAW DEVICE

BACKGROUND OF THE INVENTION

The present invention relates to a structure and a method for mounting a SAW (Surface Acoustic Wave) device to a substrate, particularly with the function surface of the SAW device facing the substrate.

It has been customary to mount a SAW device to a mounting substrate in such a manner as to maintain the function surface of the device airtight and form a preselected space over the oscillation propagation section of the device. With this configuration, it is possible to protect the function surface from extraneous interference. However, a problem with this structure is that a metal cap for implementing airtightness increases the dimension of the mounting substrate in the direction of thickness, obstructing a small size, light weight configuration. Another problem is that a sealing step is necessary and increases the number of production steps. In addition, a ceramic substrate and the metal cap increase the production cost. Although the ceramic substrate and metal cap may be replaced with plastic members in order to reduce the cost, a moistureproof feature available with plastic members is too low to fully protect comb-like electrodes called interdigital transducer (IDT) on the function surface from corrosion. This is apt to deteriorate the characteristic of the SAW device.

Japanese Patent Laid-Open Publication No. 4-150405, for example, teaches a mounting structure using a flip-chip scheme in order to reduce size and weight while enhancing airtightness. This mounting structure not including a metal cap successfully reduces size and weight. However, because the rear or top of a SAW device and its edges are sealed by silicone resin, the entire structure is greater in size than the SAW device itself. Moreover, because the silicone resin covers only the top and edges of the SAW device, temperature variation which may repeatedly act on the entire assembly brings about a stress due to a difference in the coefficient of thermal expansion between the SAW device and a substrate. The stress directly acts on the connecting portions of gold (Au) bumps. As a result, the connecting portions are apt to break due to fatigue and also apt to break when subjected to a shock or impact ascribable to, e.g., a drop. When the connecting portions break, the sealing function of the silicone resin and therefore the characteristic of the SAW device is deteriorated. Although the silicone resin may be replaced with epoxy resin which is less fragile, epoxy resin is likely to enter the gap between the function surface of the SAW device and the substrate due to surface tension, depending on the viscosity of the resin melted at the time of sealing. Such resin deposits on the oscillation propagation section of the function surface of the SAW device and prevents a space for opening the above section from being formed. Consequently, the expected characteristic of the SAW device is degraded.

Technologies relating the present invention are also disclosed in, e.g., Japanese Patent Laid-Open Publication Nos. 60-53058, 3-272212, and 4-369915.

SUMMARY OF THE INVENTION

It is therefore an object of the present invention to provide a structure capable of reliably mounting a SAW device in a small size, light weight configuration, sparingly breakable, and insuring a sealing function.

In accordance with the present invention, a structure for mounting a SAW device includes a a substrate including pads for connection. A SAW device includes a function surface on which pads for connection are positioned. The SAW device is mounted to the substrate with the function surface facing the substrate and with the pads being connected to the pads of the substrate. Photosensitive resin fills a gap between the SAW device and the substrate in the peripheral portion of the SAW device for sealing a space facing an oscillation propagation section formed on the function surface of the SAW device.

Also, in accordance with the present invention, a structure for mounting a SAW device includes a substrate including pads for connection, and a carrier substrate mounted to the substrate. A SAW device includes a function surface on which pads for connection are positioned. The SAW device is mounted to the carrier substrate with the function surface facing the carrier substrate and with the pads being connected to pads provided on the carrier substrate. Photosensitive resin fills a gap between the SAW device and the carrier substrate in the peripheral portion of the SAW device, for sealing a space facing an oscillation propagation section formed on the function surface of the SAW device.

Further, in accordance with the present invention, a method of mounting a SAW device includes the steps of forming a photosensitive resin film on a function surface included in the SAW device, patterning the photosensitive resin film by exposure and development to thereby leave the photosensitive resin film only in the peripheral portion of the SAW device, positioning the SAW device such that the function surface faces the mounting surface of a substrate, and connecting pads formed on the function surface and pads formed on the mounting surface of the substrate, and curing the photosensitive resin by heat or light.

Moreover, in accordance with the present invention, a method of mounting a SAW device includes the steps of forming a photosensitive resin film on the mounting surface of a substrate to which the SAW device is to be mounted, patterning the photosensitive resin film by exposure and development to thereby leave the photosensitive resin film only in a region corresponding to the peripheral portion of the SAW device, mounting the SAW device, having pads for connection formed on a function surface thereof, to the substrate while causing the function surface to face the mounting surface of the substrate, and connecting the pads of the SAW device to pads formed on the substrate, and curing the photosensitive resin by heat or light.

BRIEF DESCRIPTION OF THE DRAWINGS

The above and other objects, features and advantages of the present invention will become apparent from the following detailed description taken with the accompanying drawings in which.

In the figures, identical reference numerals denote identical structural elements.

DESCRIPTION OF THE PREFERRED EMBODIMENTS

Figure 1:
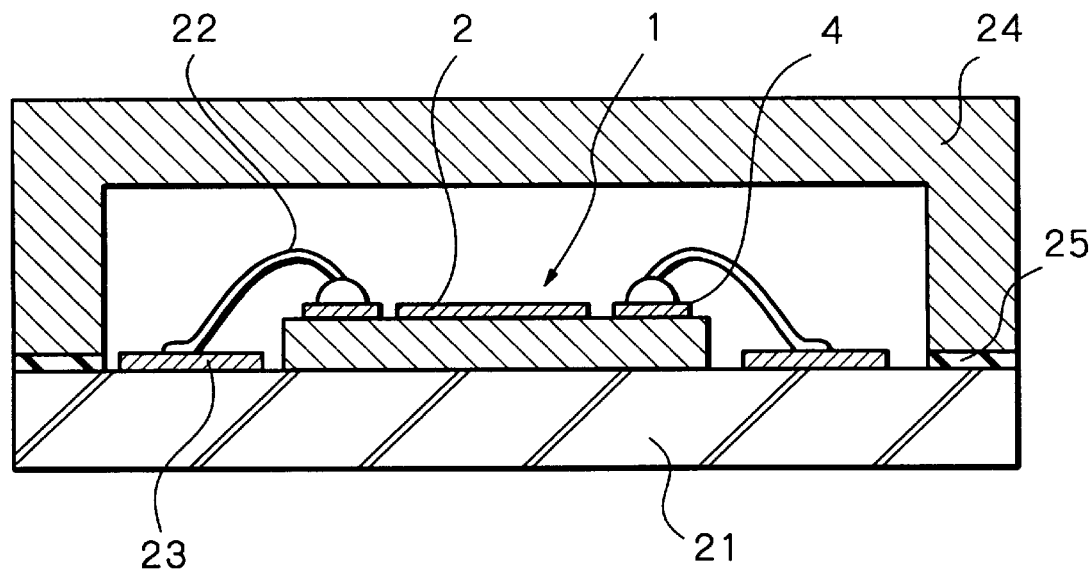
FIGS. 1 and 2 are sections each showing a particular conventional structure for mounting a SAW device.

To better understand the present invention, brief reference will be made to a conventional SAW device mounting structure, shown in FIG. 1. As shown, a SAW device 1 includes an IDT 2 formed on the front of a substrate and implemented by an Al film. With the IDT 2, the SAW device 1 performs SAW operation; the front of the device 1 constitutes a function surface. The rear of the SAW device 1 is affixed to a ceramic substrate or mounting substrate 21 by die bonding. Pads 4 formed on the front of the SAW device 1 each are electrically connected to a particular pad 23 formed on the ceramic substrate 21 by a respective wire 22. A metal cap 24 is affixed to the ceramic substrate 21 from the above. As a result, the SAW device 1 is sealed by the ceramic substrate 21 and metal cap 24. The ceramic substrate 21 is sometimes replaced with a metal substrate. The metal cap 24 is hermetically sealed by a seal 25 implemented by Kovar, gold-tin (Au—Sn) alloy or glass by way of example.

A problem with the above conventional structure is that the metal cap 24 for implementing airtightness increases the dimension of the mounting substrate in the direction of thickness, obstructing a small size, light weight configuration, as discussed earlier. Another problem is that a sealing step is necessary and increases the number of production steps. In addition, the ceramic substrate 21 and metal cap 24 increase the production cost. Although the ceramic substrate 21 and metal cap 24 may be replaced with plastic members in order to reduce the cost, a moistureproof feature available with plastic members is too low to fully protect the IDT on the function surface from corrosion. This is apt to deteriorate the characteristic of the SAW device.

Figure 2:
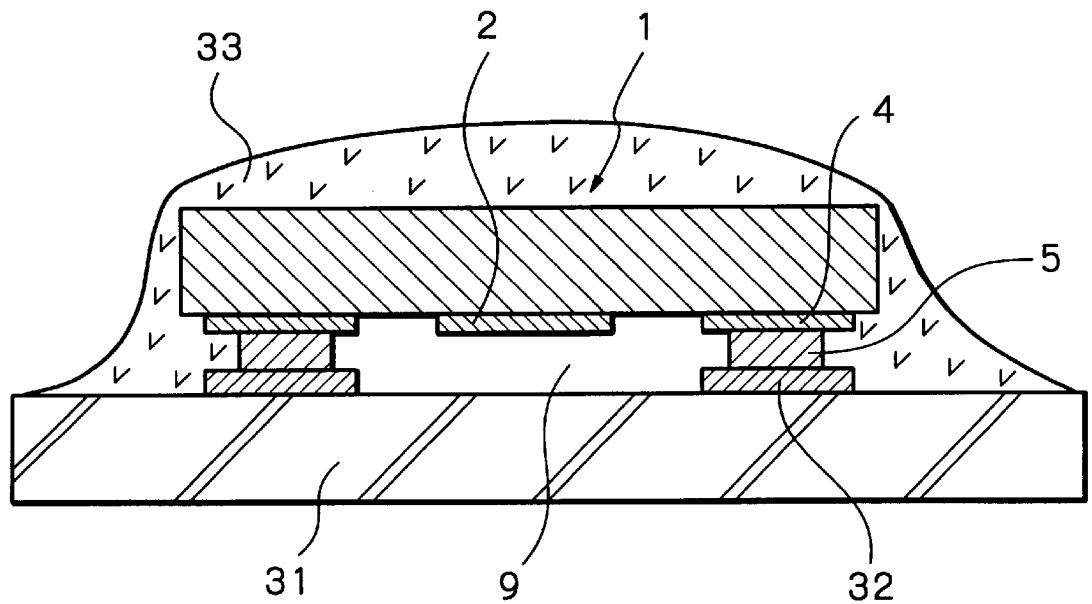

FIG. 2 shows another conventional SAW device mounting structure using a flip-chip scheme and taught in Japanese Patent Laid-Open Publication No. 4-150405 mentioned earlier. As shown, a SAW device 1 has an IDT 2 on its front or function surface. The IDT 2 is also implemented as an Al film. The SAW device 1 is positioned face down such that its function surface faces a mounting substrate 31. Pads 4 provided on the front of the SAW device 1 each is connected to a particular pad 32 provided on the mounting substrate 31 by a respective Au bump 5. Silicone resin 33 having high viscosity is fed to the above assembly by, e.g., a dispenser such that the resin 33 covers and seals the SAW device 1.

The structure shown in FIG. 2 and not including a metal cap successfully reduces the size and weight of the assembly, compared to the structure shown in FIG. 1. However, because the rear or top of the SAW device 1 and its edges are sealed by the silicone resin 33, the entire structure is greater in size than the SAW device 1 itself, as stated previously. Moreover, because the silicone resin 33 covers only the top and edges of the SAW device 1, temperature variation which may repeatedly act on the entire assembly brings about a stress due to a difference in the coefficient of thermal expansion between the SAW device 1 and the substrate 31. The stress directly acts on the connecting portions of the bumps 5. As a result, the connecting portions are apt to break due to fatigue and also apt to break when subjected to a shock or impact ascribable to, e.g., a drop. When the connecting portions break, the sealing function of the silicone resin 33 and therefore the characteristic of the SAW device 1 is deteriorated. Although the silicone resin 33 may be replaced with epoxy resin which is less fragile, epoxy resin is likely to enter the gap between the function surface of the SAW device 1 and the substrate 31 due to surface tension, depending on the viscosity of the resin melted at the time of sealing. Such resin deposits on the oscillation propagation section of the function surface of the SAW device 1 and prevents a space 9 for opening the above section from being formed. Consequently, the expected characteristic of the SAW device 1 is degraded.

Figure 3:
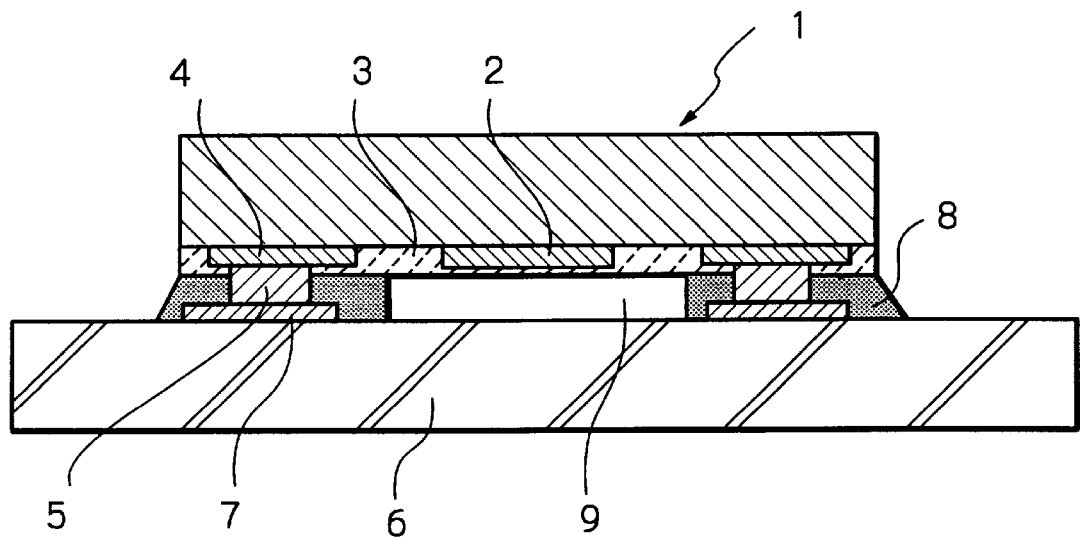
FIGS. 3–7 are sections respectively showing a first to a fifth embodiment of a SAW device mounting structure in accordance with the present invention.

Referring to FIG. 3, a first embodiment of the SAW device mounting structure in accordance with the present invention will be described. As shown, a SAW device 1 has an IDT 2 on the front of its substrate which forms a waveguide. The IDT 2 is implemented by an Al film. The front of the SAW device 1 constitutes a function surface. A 0.01 $\mu$m to 0.1 $\mu$m thick $SiO_2$ (silica) film 3 is formed on the function surface and plays the role of a protection film. Pads 4 to serve as input terminals and ground terminals are formed at preselected positions on the function surface and implemented by a part of the above Al film. Au bumps 5 are respectively formed on the pads 4. The $SiO_2$ film 3 may be formed on the entire function surface except for the pads 4, if desired. Also, $SiO_2$ may be replaced with Si, SiN or the like. The SAW device 1 is mounted on a mounting substrate 6 implemented as a glass epoxy substrate, ceramic substrate, glass substrate, flexible substrate or similar insulative substrate. Pads 7 are formed on the front of the substrate 6 in such a manner as to face the pads 4 of the SAW device 1 and are electrically connected to outside circuitry not shown.

The SAW device 1 is mounted to the substrate 6 face down, i.e., with its function surface facing the front of the substrate 6. The Au bumps 5 are positioned on the corresponding pads 7 of the substrate 6 and then heated and pressed to be mechanically and electrically affixed to the pads 7. Photosensitive resin 8 is filled in the gap between the SAW device 1 and the substrate 6 except for the function surface. That is, the resin 8 is filled in a frame-like region surrounding the function surface of the SAW device 1. The resin 8 therefore seals the gap formed between the SAW device 1 and the substrate 6 by the Au bumps 5 and pads 4 and 7. Further, a space 9 is formed between the function surface of the SAW device 1 and the substrate 6. The space 9 plays the role of a space for opening the oscillation propagation section of the SAW device 1 and guarantees the characteristic of the device 1.

For the photosensitive resin 8, use is made of thermosetting resin or photocuring resin having, after setting or curing, a glass transition point of 300° C. higher than the melting point of eutectic solder which is 183° C. While the glass transition point should only be between 200° C. and 310° C., it may be lower than 200° C. inclusive if heat resistivity is not required. Further, the resin 8 is expected to have a coefficient of thermal expansion of $70 \times 10^{-6}$/° C. without a filler. The coefficient of thermal expansion is adjustable within the range of 22 to $70 \times 10^{-6}$/° C. by the addition of $SiO_2$ or similar filler.

In the above structure, the SAW device 1 and substrate 6 are affixed together only by the photosensitive resin 8 intervening between them. The substrate 6 can therefore be reduced in dimension in the direction of height to substantially the same size as the SAW device 1 and can be reduced in weight also. The resin 8 extending along the periphery of the SAW device 1 in the form of a frame seals the function surface of the device 1, particularly the peripheral portion of the oscillation propagation section. This prevents water and dust from entering the oscillation propagation section and thereby insures the expected characteristic of the SAW device 1. Even if water or dust reaches the function surface through the resin 8, the SiO2 film or protection film 3 existing on the function surface reduces the corrosion of the IDT 2. Furthermore, although temperature variation may repeatedly act on the assembly, the resulting stress ascribable to a difference in the coefficient of thermal expansion between the SAW device 1 and the substrate 6 is partly absorbed by the resin 8. As a result, the bumps 5 are subjected to a minimum of stress and therefore protected from breakage ascribable to fatigue. In addition, the connecting portions of the bumps 5 are free from breakage ascribable to a shock or impact.

Figure 8:
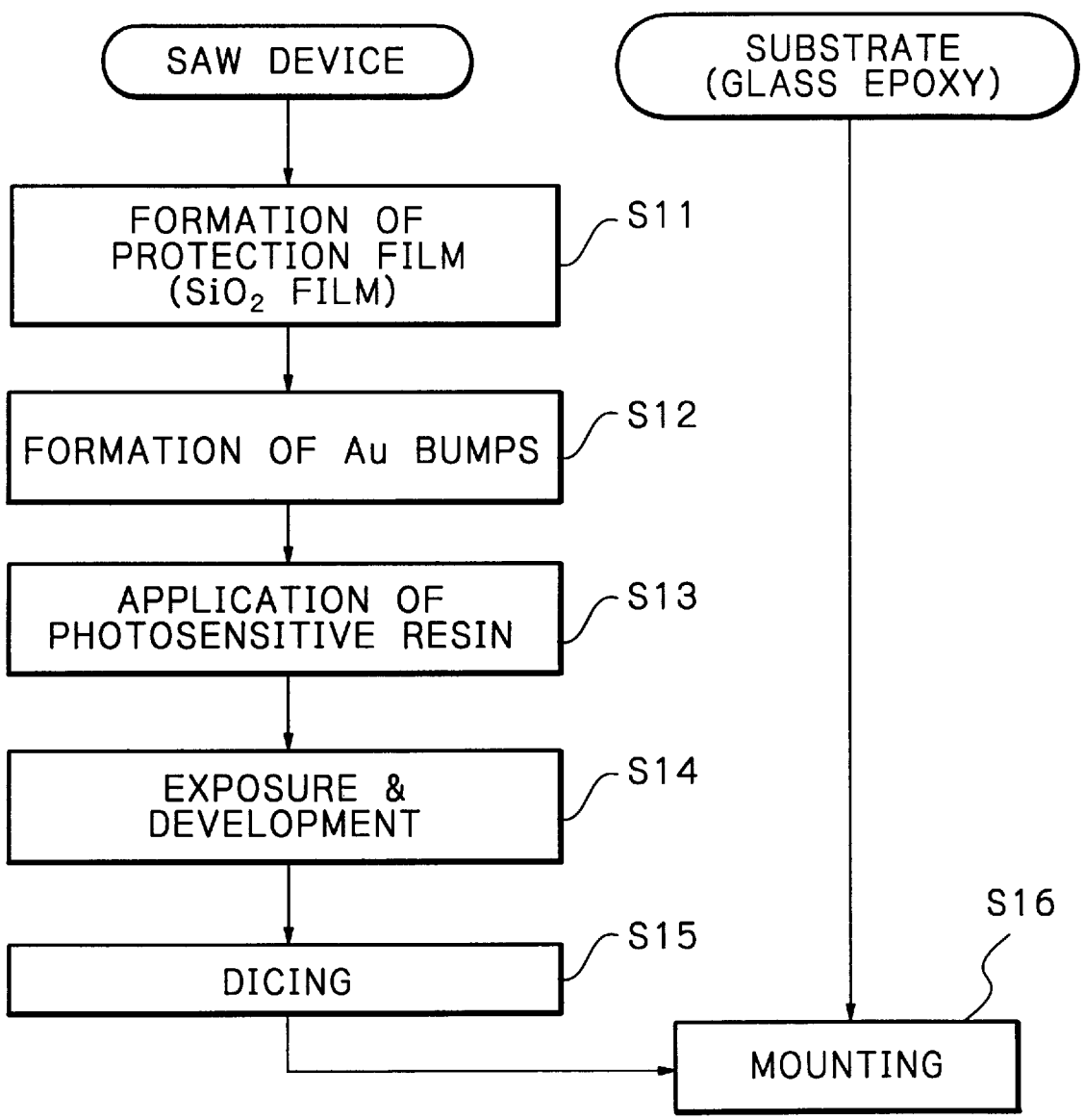
FIG. 8 is a flowchart demonstrating a method for implementing the structure shown in FIG. 3 or 4.

FIG. 8 is a flowchart demonstrating a method of constructing the assembly shown in FIG. 3. First, the SAW device 1 with the IDT 2 and pads 4 is prepared in the form of a wafer together with other SAW devices. Then, the SiO2 film or protection film 3 is formed on the function surface of each SAW device 1 (step S11). The Au bumps 5 are formed on the pads 4 by plating, wire bonding, transfer bump method or similar technique (step S12). The Au bumps 5 should preferably be provided with the same height by leveling beforehand. Subsequently, the photosensitive resin 8 is applied to the entire wafer to a thickness of 10 μm to 100 μm by spin coating, printing or similar technology (step S13). At this instant, the resin 8 should preferably be provided with a thickness which will substantially coincide with the height of the Au bumps 5 when the SAW device 1 is mounted to the substrate 6. The part of the resin 8 existing in the oscillation propagation section including the IDT 2 is selectively removed by exposure and development, so that the resin 8 is left only in the peripheral portion of the SAW device 1 (step S14). Thereafter, such SAW devices 1 in the form of a wafer are separated from each other by dicing (step S15). After each SAW device 1 has been positioned face down, the Au bumps 5 are respectively positioned on the pads 7 of the substrate 6. Then, the SAW device 1 is heated to 200° C. or above while being pressed toward the substrate 6 by a pressure of 30 g to 150 g for a bump. As a result, the Au bumps 5 are affixed to the corresponding pads 7 while the resin 8 is cured by heat, affixing the SAW device 1 to the substrate 6 (step S16).

The procedure described above provides the photosensitive resin 8 with a desired pattern by exposure and development. Further, the fluidity of the resin 8 undergone development is so low, the resin 8 does not flow at the time of mounting by contrast to the conventional epoxy resin. It follows that when the SAW device 1 is mounted to the substrate 6, the space 9 corresponding to the oscillation propagation section of the device 1 can be formed with accuracy. This stabilizes the characteristic of the SAW device 1 after the mounting procedure.

A second embodiment of the present invention will be described with reference to FIG. 4. As shown, this embodiment is identical with the first embodiment except that the photosensitive resin 8 is formed in the peripheral portion not including the pads 4 and 7 or Au bumps 5. This configuration achieves the same advantages as the first embodiment. However, because the resin 8 does not cover the Au bumps 5, the stress reducing effect is slightly reduced. The second embodiment is therefore practicable when the difference in the coefficient of thermal expansion between the SAW device 1 and the substrate 6 is small enough to reduce the stress to act on the connecting portions of the Au bumps 5. The resin 8 does not obstruct the connection of the SAW device 1 to the substrate 6 through the Au bumps 5.

Figure 4:
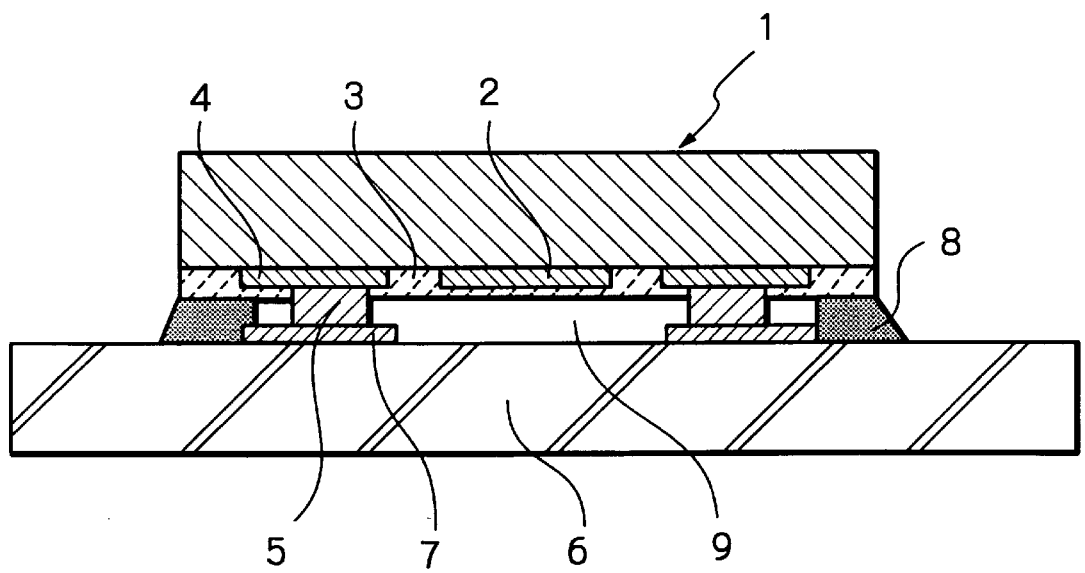
Figure 9:
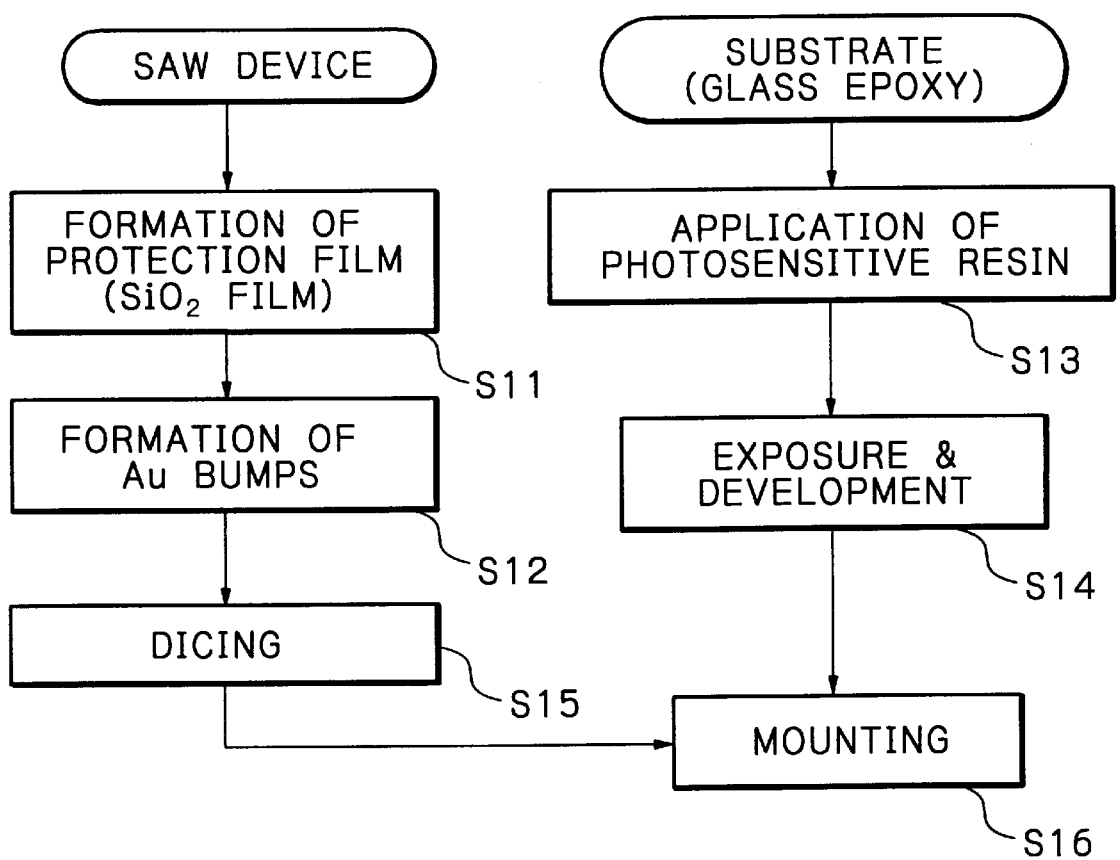
FIG. 9 is a flowchart demonstrating another method for implementing the structure of FIG. 3 or 4.

FIG. 9 is a flowchart representative of another procedure for implementing the structure of FIG. 3 or 4. As shown, after the formation of the protection film 3 on each SAW device 1 (step S11) and the formation of the Au bumps 5 (step S12), the SAW devices 1 are separated from each other by dicing (step S15). In parallel with such steps, the photosensitive resin 8 is applied to the entire surface of the substrate 6 (step S13). Then, the resin 8 is exposed and developed such that it remains in the required region of the substrate 6, i.e., the region which will face the peripheral portion of the SAW device 1 at the time of mounting (step S14). Subsequently, the SAW device 1 is mounted to the substrate 6 (step S16). Thus, the resin 8 can be formed on the substrate at the same time as the SAW device 1 is fabricated. Therefore, the SAW device 1 should only be directly mounted to the substrate 6, as in the conventional procedure.

Figure 5:
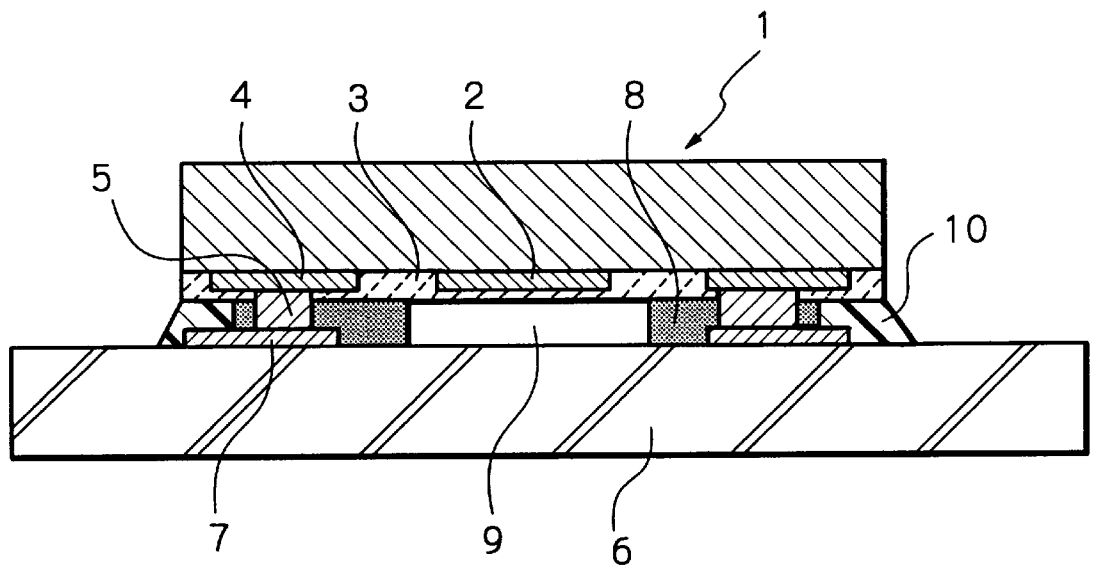

Reference will be made to FIG. 5 for describing a third embodiment of the present invention. As shown, second resin 10 surrounds the photosensitive resin 8 intervening between the SAW device 1 and the substrate 6. The second resin 10 may be either insulative or conductive and may cover only the portions of the SAW device 1 and substrate 6 facing each other or the side faces of the SAW device 1. When the resin 10 covers the side faces of the SAW device 1, it may be extended to the rear of the device 1.

In the structure shown in FIG. 5, only if the resin 10 is adequately selected, the oscillation propagation section of the SAW device 1 can be more surely sealed with the resin 10 surrounding the photosensitive resin 8 than with the resin 8 alone. This obviates the entry of water more effectively. When a conductive layer is provided on the rear (top in FIG. 5) of the SAW device 1, the resin 10 may be implemented by conductive resin in order to electrically connect the rear of the device 1 and any desired wiring of the substrate 6. The conductive resin allows the rear of the SAW device 1 to be held at any desired potential and thereby enhances the electrical characteristic and stability of the device 1.

To implement the structure of FIG. 5, after the SAW device 1 shown in FIG. 3 or 4 has been mounted to the substrate 6 or after all the mounting steps have completed, the second resin 10 is fed to the outer periphery of the photosensitive resin 8 by, e.g., a dispenser. The resin 10 is cured by either heat or light, as needed.

Figure 6:
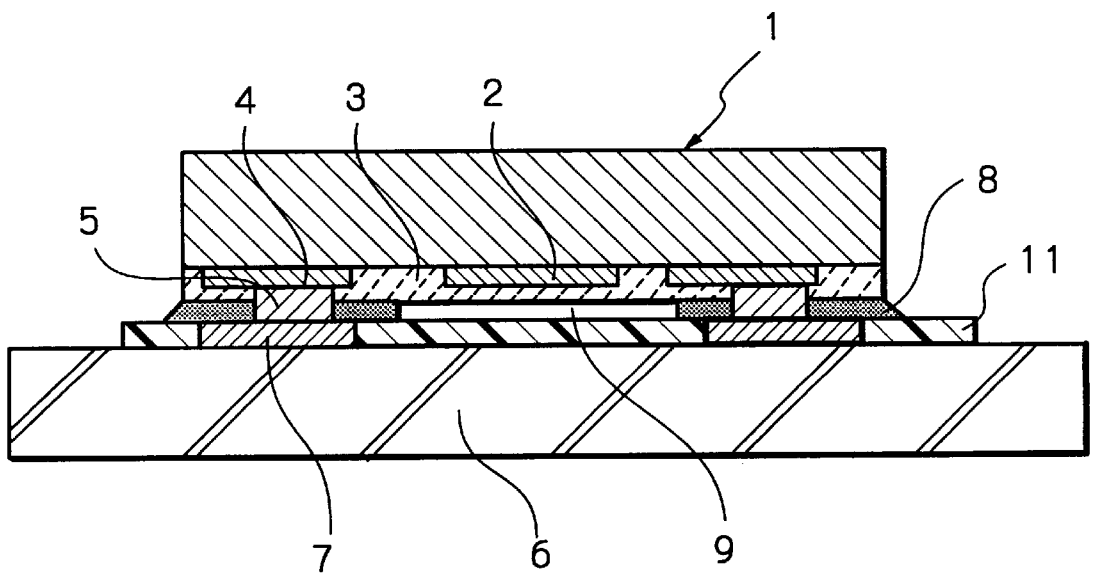

FIG. 6 shows a fourth embodiment of the present invention. As shown, the photosensitive resin 8 and second resin 11 is provided between the SAW device 1 and the substrate 6 in a laminate structure. In this embodiment, the resin 8 is positioned in a region containing the Au bumps 5 and provided with a thickness substantially equal to the height of the bumps 5. The resin 11 surrounds the pads 7 and has substantially the same thickness as the pads 7 of the substrate 6. Therefore, when the SAW device 1 is mounted to the substrate 6, the resins 8 and 11 are bonded to each other and seal the oscillation propagation section of the device 1.

The structure shown in FIG. 6 is produced by the following procedure. The photosensitive resin 8 is selectively formed on the SAW device 1 while the second resin 11 is selectively formed in the preselected region of the substrate 6 in parallel with the formation of the resin 8. Subsequently, the SAW device 1 is mounted to the substrate 6. The resin 11 may be applied to the surface of the substrate 6 in the form of a liquid or a paste by dispensing, printing or similar technology. Alternatively, the resin 11 implemented as a sheet having a preselected pattern may be adhered to the surface of the substrate 6.

Figure 7:
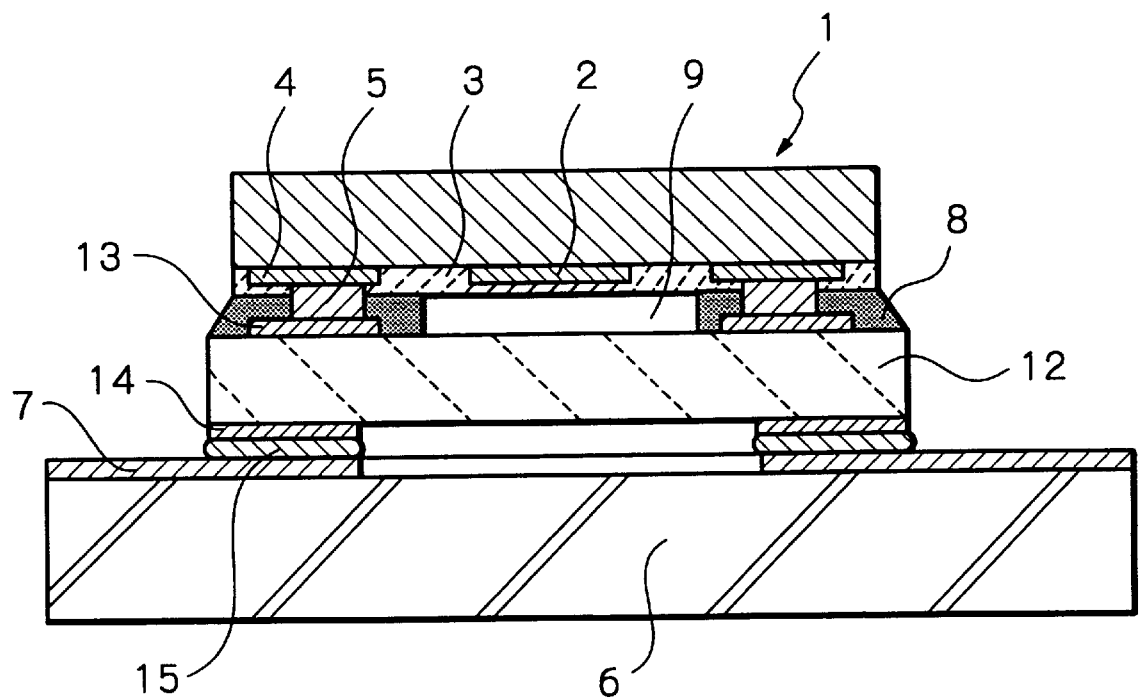

FIG. 7 shows a fifth embodiment of the present invention. As shown, the SAW device 1 is mounted on a carrier substrate 12 having substantially the same size as the device 1. While the SAW device 1 may be mounted to the carrier substrate 12 in any one of the configurations of the above embodiments, the configuration of the first embodiment is used in this embodiment. Specifically, the pads 4 of the SAW device 1 and pads 13 formed on the carrier substrate 12 are bonded together by the Au bumps 5. The photosensitive resin 8 fills the gap between the peripheral portion of the SAW device 1 and that of the carrier substrate 12 and including the Au bumps 5, sealing the space 9 for sealing the oscillation propagation section of the device 1. Although this configuration slightly increases the dimension of the SAW device 1 and carrier substrate 12 subassembly by the thickness of the substrate 12, the substrate 12 is thin enough to render the subassembly as thin as the SAW device 1.

The carrier substrate 12 with the SAW device 1 is mounted to the substrate 6. At this instant, pads 14 formed on the rear of the carrier substrate 12 are connected to the pads 7 of the substrate 6 through solder bumps 15. Resin may be filled between the carrier substrate 12 and the substrate 6 in order to enhance reliable connection through the solder bumps 15. For the carrier substrate 12, use may be made of a glass epoxy substrate, ceramic substrate, glass substrate, flexible substrate or polyimid substrate. Also, the carrier substrate 12 and substrate 6 may be connected together by a land scheme, leadless chip carrier scheme or similar scheme in place of the metal bump scheme.

The second resin included in the third embodiment may also be applied to any one of the second, fourth and fifth embodiments. In the third and fifth embodiments, the photosensitive resin may be formed in the region not including the Au bumps, as in the second embodiment.

In the illustrative embodiments, the comb electrode and pads are implemented by an Al film which is inexpensive and easily implements the characteristic required of the SAW device 1. If desired, the Al film may be replaced with any other suitable conductive film. The Au bumps used to connect the pads of the SAW device 1 and those of the substrate may be replaced with solder bumps or similar metal bumps or a combination of a plurality of different metal bumps.

In summary, it will be seen that the present invention provides a structure and a method for mounting a SAW device having various unprecedented advantages, as enumerated below.

(1) Use is made of photosensitive resin for guaranteeing a space for the oscillation propagation section included in the function surface of a SAW device. This, coupled with the fact that the resin seals the above space while filling the gap between the peripheral portion of the SAW device and that of a substrate, the mounting structure is as small in size as the SAW device and light weight and does not effect the characteristic of the SAW device.

(2) Second resin is added to further enhance the sealing effect.

(3) The photosensitive resin is formed in a region including connecting pads connecting the SAW device and mounting pads. The resin therefore reduces a thermal stress and a stress ascribable to a shock or impact and apt to act on the connecting pads, thereby enhancing reliable connection.

(4) A protection film formed on the function surface of the SAW device prevents electrodes from being corroded and the characteristic of the SAW device from being deteriorated by water, dust and other impurities.

(5) The photosensitive resin between the SAW device and the substrate can be provided with any desired pattern by exposure and development. In addition, the resin is cured by heat or light in order to connect the SAW device and the substrate. Such a mounting method is easier to practice than the conventional mounting method. Further, there can be guaranteed the space for the oscillation propagation section of the SAW device and the easy patterning of the resin in a desired region, e.g., a region including or not including the connecting pads.

Various modifications will become possible for those skilled in the art after receiving the teachings of the present disclosure without departing from the scope thereof.

What is claimed is:

1. A structure for mounting an electronic device, said structure comprising:
   a substrate including substrate pads for connection;
   a SAW (Surface Acoustic Wave) device including a function surface on which surface pads for connection are positioned, said SAW device being mounted to said substrate with said function surface facing said substrate and with said surface pads being connected to said substrate pads of said substrate; and
   a photosensitive resin filling a gap between said SAW device and said substrate in a peripheral portion of said SAW device, for sealing a space adjacent an oscillation propagation section formed on said function surface of said SAW device,
   wherein said gap is filled by said photosensitive resin so that said photosensitive resin secures said SAW device to said mounting substrate.

2. A structure as claimed in claim 1, wherein said photosensitive resin is formed in a region including said pads of said SAW device and said pads of said substrate.

3. A structure as claimed in claim 1, wherein said photosensitive resin is formed in a region surrounding said pads of said SAW device and said pads of said substrate.

4. A structure as claimed in claim 1, further comprising a second resin surrounding said photosensitive resin.

5. A structure as claimed in claim 1, wherein a second resin is filled around said photosensitive resin.

6. A structure as claimed in claim 1, wherein said substrate further comprises a second resin layered on said substrate, and wherein said photosensitive resin is stacked on said second resin.

7. A structure as claimed in claim 6, wherein said photosensitive resin has a glass transition point between 200° C. and 310° C. after curing.

8. A structure as claimed in claim 6, wherein said photosensitive resin has a coefficient of thermal expansion between $50 \times 10^{-6}/°$ C. and $75 \times 10^{-6}/°$ C. after curing.

9. A structure as claimed in claim 1, wherein said pads of said SAW device and said pads of said substrate are connected by metal bumps.

10. A structure as claimed in claim 1, wherein said SAW device includes a protection film covering at least a part of said function surface.

11. A mounting structure comprising:
    a substrate including substrate pads for connection;
    a carrier substrate mounted to said substrate;
    a SAW (Surface Acoustic Wave) device including a function surface on which surface pads for connection are positioned, said SAW device being mounted to said carrier substrate with said function surface facing said carrier substrate and with said surface pads being connected to carrier pads provided on said carrier substrate; and
    a photosensitive resin filling a gap between said SAW device and said carrier substrate in a peripheral portion of said SAW device, for sealing a space adjacent an oscillation propagation section formed on said function surface of said SAW device,
    wherein said gap is filled by said photosensitive resin so that said photosensitive resin secures said SAW device to said carrier substrate.

12. A structure as claimed in claim 11, wherein said SAW device includes a protection film covering at least a part of said function surface.

* * * * *